United States Patent [19]
Edgren et al.

[11] Patent Number: 5,204,116
[45] Date of Patent: Apr. 20, 1993

[54] DOSAGE FORM PROVIDING IMMEDIATE THERAPY FOLLOWED BY PROLONGED THERAPY

[75] Inventors: David E. Edgren, El Granada; Gurdish K. Bhatti, Fremont; Judy A. Magruder, Mountain View, all of Calif.

[73] Assignee: Alza Corporation, Palo Alto, Calif.

[21] Appl. No.: 694,173

[22] Filed: May 1, 1991

[51] Int. Cl.$^5$ ............................................. A61K 9/24
[52] U.S. Cl. .................................. 428/473; 424/472; 424/468
[58] Field of Search ................... 424/473, 468, 472

[56] References Cited

U.S. PATENT DOCUMENTS

| | | | |
|---|---|---|---|
| 3,870,790 | 3/1975 | Lowey et al. | 424/19 |
| 4,140,755 | 2/1979 | Sheth et al. | 424/21 |
| 4,167,558 | 9/1979 | Sheth et al. | 424/22 |
| 4,226,849 | 10/1980 | Schor | 424/19 |
| 4,259,314 | 3/1981 | Lowey | 424/19 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,540,566 | 9/1985 | Davis et al. | 424/22 |
| 4,571,333 | 2/1986 | Hsiao et al. | 424/22 |
| 4,662,880 | 5/1987 | Hamel et al. | 424/467 |
| 4,680,323 | 7/1987 | Lowey | 524/23 |
| 4,786,503 | 11/1988 | Edgren et al. | 424/443 |
| 4,810,502 | 3/1989 | Ayer et al. | 424/473 |
| 4,849,229 | 7/1989 | Gaylord | 424/468 |
| 4,915,952 | 4/1990 | Ayr et al. | 424/417 |
| 4,946,685 | 8/1990 | Edgren et al. | 424/472 |

Primary Examiner—Thurman K. Page
Assistant Examiner—Leon R. Horne
Attorney, Agent, or Firm—Paul L. Sabatine; Edward L. Mandell; Jean M. Duvall

[57] ABSTRACT

A dosage form is disclosed comprising a first layer and a second layer. The first layer provides immediate therapy and comprises a drug stereoisomer and the second layer provides prolonged therapy and comprises a drug racemate.

4 Claims, 2 Drawing Sheets

DOSAGE FORM PROVIDING IMMEDIATE THERAPY FOLLOWED BY PROLONGED THERAPY

FIELD OF THE INVENTION

This invention pertains to a biologically acceptable dosage form for providing immediate therapy followed by prolonged therapy. More particularly, the invention relates to a dosage form comprising a first layer for immediate therapy, which first layer comprises a cellulosic polymer and a therapeutically active drug stereoisomer, and a second layer for prolonged therapy, which second layer comprises a cellulosic polymer and a therapeutically active drug racemate. The invention concerns also a method for immediate therapy comprising administering a stereoisomer drug followed by prolonged therapy comprising the administration of a racemic drug to a warm-blooded animal in need of therapy.

BACKGROUND OF THE INVENTION

Dosage forms manufactured as a compressed, single-layer tablet comprising a cellulose polymer and a racemic drug mixture are known to the drug dispensing art. For example, such a single-layered dosage form is disclosed in the following references: U.S. Pat. No. 3,870,790 issued to Lowey et al; U.S. Pat. No. 4,140,755 issued to Sheth et al; U.S. Pat. No. 4,167,558 issued to Sheth et al; U.S. Pat. No. 4,226,849 issued to Schor; U.S. Pat. No. 4,259,314 issued to Lowey; U.S. Pat. No. 4,357,469 issued to Schor; U.S. Pat. No. 4,369,172 issued to Schor et al; U.S. Pat. No. 4,389,393 issued to Schor et al; U.S. Pat. No. 4,540,566 issued to Davis et al; U.S. Pat. No. 4,571,333 issued to Hsiao et al; U.S. Pat. No. 4,680,323 issued to Lowey; and U.S. Pat. No. 4,849,229 issued to Gaylord et al. A dosage form manufactured as a bilayered tablet comprising a cellulose polymer and a racemic drug mixture is disclosed in the following references: U.S. Pat. No. 4,786,503 issued to Edgren et al; and U.S. Pat. No. 4,946,685 issued to Edgren et al.

While the dosage forms known to the prior art provide for delivering a racemic drug mixture, they do not provide for delivering a single, stereoisomer drug. Stereoisomers are molecules comprising atoms uniquely oriented in space. Stereoisomers as compounds were first discovered by a mineralogist named Biot in 1815. About 30 years later, Pasteur observed that certain stereoisomers, called optical isomers, had a mirror-image relationship. Thirty years passed from then until a theory was proposed by van't Hoff and LeBel to account for the optical activity of such compounds, based on the asymmetrical bonding around a carbon atom. Fifty years then passed before systematic studies were reported by Cushny on the pharmacological effects of some naturally occurring optical isomers. About 10 years later, in 1933, Easson and Stedman proposed a hypothesis to account for differences between effects of optical isomers. Since then, attention has been given to the role of spatial configuration in the effects of drugs. The stereoisomer drug generally differs in increased pharmacodynamic and pharmacokinetic properties attributed to drugs stereoselective interaction with the biological macromolecules, as reported in *Handbook of Stereoisomers*, by Smith, page 1, (1989), published by CRC Press, Inc., Boca Raton, Fla., and in *J. Pharmaceutical Sciences*, Vol. 78, page 695, (1989).

The dosage forms known to the above prior art for delivering a racemic drug mixture possess major shortcomings and they are in need of inventive improvement. For example, the prior art dosage forms deliver excess and unneeded drug as these forms deliver a racemic mixture of the drug and they do not provide for delivering the more physiologically-active stereoisomer of the drug. The prior art single layer dosage forms deliver the racemic mixture of the drug and these dosage forms lack the means for delivering independently the more active stereoisomer of the drug. Another shortcoming is the prior art bilayer form does not provide for immediate therapy at an enhanced level achieved by delivering the more active stereoisomer first, followed by the continuous and prolonged delivery of the drug racemate. Also, the prior art dosage forms do not provide that a drug molecule in its more physiologically active form can be delivered free of interaction with the dosage form to a biological, stereoselective drug receptor for quick and increased drug therapy.

In light of the above presentation, it will be appreciated by those versed in the dispensing art, that if a novel dosage form is made available to the medical, veterinary and pharmaceutical arts, that overcomes the shortcomings known to the prior art, such a dosage form would have a definite use and it would also be a valuable contribution to the dispensing art. It will be appreciated further by those versed in the dispensing art that if a dosage form can be provided that (a) possesses the ability to deliver a drug stereoisomer, followed by (b) the ability to deliver a racemate of the drug, and which dosage form (c) can be manufactured at an economical cost, such a dosage form would have a positive and practical value, and it would also represent an advancement in the pharmaceutical, medical and veterinary arts.

OBJECT OF THE INVENTION

Accordingly, it is an immediate object of this invention to provide a novel dosage form that overcomes the shortcomings known to the prior art.

Another immediate object of this invention is to provide a novel dosage form for the controlled delivery of a therapeutically active stereoisomer drug to a biological environment of use, wherein the dosage form represents an improvement and an advancement in the drug delivery art.

Another object of the invention is to provide a dosage form comprising a first layer and a second layer, wherein the first layer comprises a drug stereoisomer and wherein the second layer comprises a drug racemate.

Another object of this invention is to provide a dosage form comprising a first layer comprising a drug stereoisomer and a cellulosic composition, which first layer releasably stores the stereoisomer substantially free of interaction and adverse effect from the cellulosic composition.

Another object of this invention is to provide a dosage form comprising a first layer comprising a drug stereoisomer and a second layer comprising a drug racemate, which first and second layers comprise a cellulosic polymer that releasably stores and delivers the stereoisomer first and then, the racemate second, and which first and second deliveries occur substantially free of interacting and substantially free of binding with the cellulosic polymer.

Another object of the invention is to provide a dosage form that can deliver a beneficial drug stereoisomer that is difficult to deliver and now can be delivered by the dosage form of this invention at an immediate rate to a biological receptor.

Another object of the present invention is to provide a novel dosage form comprising a beneficial drug stereoisomer that can be from soluble to very soluble in an aqueous fluid, and which drug can be stored and delivered by the dosage form at an in vitro instant rate or release that is paralleled by an in vivo instant rate of release.

Another object of this invention is to provide a dosage form that can administer to a warm-blooded host a complete pharmaceutical regimen comprising a poorly soluble to a very soluble stereoisomer drug at an instant rate of release, followed by a poorly soluble to a very soluble racemic drug composition at a controlled and continuous rate for a particular time period, the use of which dosage form requires intervention only for initiation and possible termination of the regimen.

Another object of the present invention is to provide a dosage form for delivering a drug in the gastrointestinal tract that substantially avoids a premature break-up in the gastrointestinal tract, and which dosage form delivers immediately the physiologically active stereoisomer also known as the enantiomer in a period up to 1 hour, and then over a period up to 24 hours a racemic mixture comprising the two drug enantiomers.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawing figures, which are not drawn to scale, but are set forth to illustrate various embodiments of the invention, the drawing figures are as follows.

In the drawing figures and in the specification like parts in related figures are identified by like numbers. The term appearing earlier in the specification and in the drawing figures, as well as embodiments thereof, are further described elsewhere in this specification.

DETAILED DESCRIPTION OF THE DRAWING FIGURES

Figure 1:
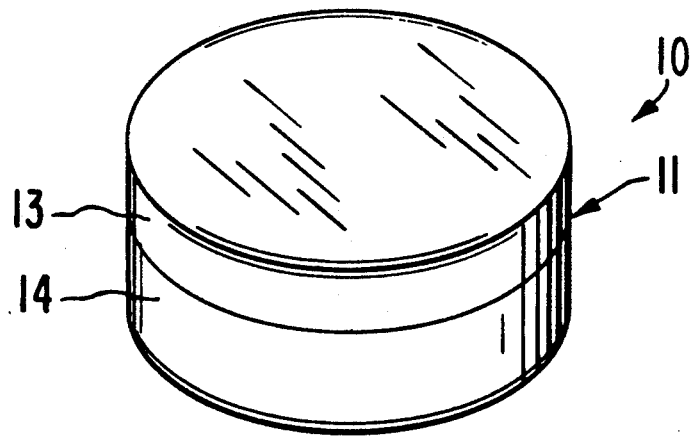
FIG. 1 is a view of a dosage form provided by the invention, which dosage form is sized and shaped for orally administering a stereoisomer independently and a racemate to the gastrointestinal tract of a drug recipient.

Turning now to the drawing figures in detail, which drawing figures are an example of the dosage forms provided by the invention, and which examples are not to be construed as limiting, one example of the dosage form is illustrated in FIG. 1 by the numeral 10. In FIG. 1, dosage form 10 comprises a body 11. Dosage form 10 can be manufactured into various sizes and shapes adapted for oral admittance into the gastrointestinal tract of a warm-blooded animal. For example, dosage form 10 can be manufactured into any convenient shape, such as ellipsoid, bean-shaped, circular-shaped, square-shaped, rectangular-shaped, capsule-shaped, and caplet-shaped.

Figure 2:
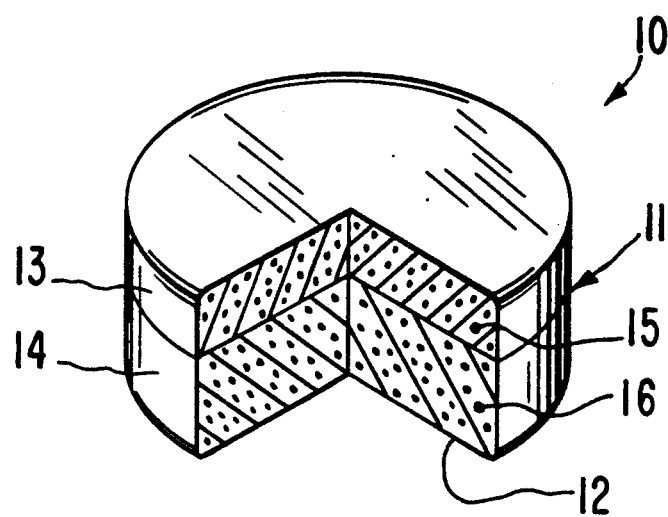
FIG. 2 is an opened view of the dosage form of FIG. 1, which opened view illustrates the internal bilayer structure of the dosage form comprising a first layer comprising a stereoisomer and a second layer comprising a racemate.

In drawing FIG. 2, dosage form 10 is manufactured optionally as a round tablet for easy oral administration to an animal. In the drawing, dosage form 10 is seen in opened section at 12. In FIG. 2, dosage form 10 comprises a body 11, which body comprises a bilayer core. The bilayer core comprises a first layer 13 and a second layer 14. Initially, first layer 13 and second layer 14 are in layered contacting arrangement, and the two layers operate in concert to provide both immediate therapy and prolonged therapy from a single dosage form, that administers two different therapeutic compositions, the instant therapy composition and the prolonged therapy composition. Dosage form 10, in first layer 13, comprises at least one drug 15 in stereoisomer form, and it is the immediate release rate layer. The expression immediate release rate layer, as used for the purpose of this invention, means drug 15 is released in a period of time comprising instant release up to 1 hour. Dosage form 10 comprises in second layer 14, drug 16 present as a racemic composition. Second layer 14 is a prolonged release rate layer. The expression "prolonged release rate layer", as used for the purpose of this invention, means racemic drug 16 is released in a period of time comprising one-half hour up to 24 hours. Also, optionally, other pharmaceutically acceptable layer-forming ingredients can be present in first layer 13 and in second layer 14.

The term "stereoisomer" and the term "racemate", are used for the purpose of this invention, to denote drug 15 in first layer 13 and drug 16 in second layer 14 pertains to the chirality of a drug. The chirality of a drug denotes that a drug exists in molecular form called enantiomers. Enantiomers are distinguished by their ability to rotate the plane of polarized light. One enantiomer rotates the plane of light to the right, (called dextrorotatory, d or +), while the other enantiomer rotates the plane of light to the left, (levorotatory, l or −). Enantiomers, for the purpose of this invention are called stereoisomers, and the invention pertains to a therapeutically active stereoisomer in the first layer, and a mixture of stereoisomers called racemate in the second layer. The racemate comprises a therapeutically active stereoisomer and a lesser or nonactive stereoisomer. The racemic mixture comprises an equal number of (+) and (−) stereoisomer molecules. The racemic mixture is essentially free of optical activity. The dosage unit amount of therapeutically active stereoisomer drug 15 in first layer 13 is 0.10 ng to 500 mg. The dosage unit amount of therapeutically active racemate 16 in second layer 14 is 1 mg to 650 mg. A discussion of stereoisomers, racemates, their preparation and isolation are reported in *Chem. and Eng. News*, pages 9–14, (Jul. 9, 1990); *Acta Pharm. Nord.*, Vol. 2, No. 3, pages 193–196, (1990); *Basic Principles of Organic Chemistry*. by John D. Roberts et al., pages 589-593, (1965) published by Benjamin-Cummings Inc.; *Fundamentals of General Organic Biological Chemistry*, by John Holum, p. 429, (1978), published by John Wiley Press, Inc.; and, *Drug Information Journal*, Vol. 24, pages 117-120, (1990).

The dosage form provided by this invention for the administration of the stereoisomer drug followed by the administration of the racemate drug provides unexpected therapeutic advantages. For example, the immediate release layer 13 administers stereoisomer drug 14 in its most potent isomeric form for causing a rapid absorption of drug 14 which quickly produces therapeutic plasma levels. The faster the immediate layer 13 releases stereoisomer drug 14, the more quickly stereoisomer drug 14 is available or absorption and the quicker the patient benefits therapeutically. Following this initial therapy, the prolonged-release layer 14 releases racemic drug 16 for maintaining the desired therapeutic blood levels for a prolonged period of time. The instant release rate layer and the prolonged release rate layer are physically and chemically compatible thereby providing for the release of the stereoisomer drug and the racemic drug essentially free of unwanted influence on the respective drugs. The present invention administers the drugs substantially free from unwanted effects of the cellulosic polymers comprising the dosage form.

Dosage form 10 comprises a therapeutic isomeric drug, composition and a therapeutic racemic drug composition. In this specification, and in the accompanying claims, the term "drug" includes any physiologically or pharmacologically active substance that produces a local or a systemic effect in animals, which includes warm-blooded mammals, humans, primates, avians, household animals, sport animals, farm animals, laboratory animals, fishes, reptiles and zoo animals. The term "physiologically" as used herein, denotes the administration of a drug to produce generally normal levels and functions in a warm-blooded animal, and the term "pharmacologically" generally denotes response to the amount of drug administered to the host. See, *Medical Dictionary*, by Stedman, 1966, published by Williams and Wilkins, Baltimore, Md.

The therapeutically active drugs that can be delivered by dosage form 10 comprise inorganic and organic drugs. The drugs include drugs that act on peripheral nerve, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, organ systems, body passageways, reproductive system, skeletal system, autocoid systems, alimentary and excretory systems inhibitors of autocoids and histamine systems. The drug that can be delivered for acting on these recipients include anticonvulsants, analgesics, anti-parkinsons, anti-inflammatories, anesthetics, antimicrobials, antimalarials, antiparasitic, antihypertensives, angiotensin converting enzyme inhibitor, antihistamines, antipyretics, alpha-adrenergic agonist, alpha-blockers, biocides, bactericides, bronchial dilators, beta-adrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, and vitamins.

The stereoisomer drug 15 comprising a stereoisomer drug neat, and the racemic drug 16, comprising a pair of two different stereoisomers that can be used according to the mode and the manner of this invention comprise a member or a pair of (+) and (−) stereoisomers selected from the group consisting of the following: acenocoumarin anticoagulant; acetyl-alpha-methyl-choline cholinergic; acetyl-beta-methyl-choline cholinergic; alprenolol antiarrhythmic; atenolol; (d) brompheniramine; bupivacaine captopril; carbuterol; chlorpheniramine; ciramadol; dibozane; dimethindene, 5-(1,3 dimethylbutyl)-5-ethyl barbituric acid; dobutamine; levo-dopa; dyphylline; estrone; etodolac; fenoprofen; fentanyl; hexobarbital; hyoscyamine; ibuprofen; idazoxan; indacrinone; indacrinone; indomethacin; ketamine; ketorolac; labetative; levamisole/tetramisole; mabuterol; mequitazine; methacholine; methadone; methyldopamine; methylnorepinephrine; metoprolol; mianserin; naproxen; nimodipine; penicillamine; pentazocine; pentobarbital; pheniramine; phenoxybenzamine; phenylephrine; prinadol; picenadol; piperoxan; practolol; prizidilol; procaterol; propranolol; prosympal; reproterol; selegiline; sotalol; soterenol; sulindac; terbutaline; thyroxine; tilidine; timolol; tocainide; and warfarin. The isomers additionally comprise epinephrine; ketoprofen; noradrenaline; norepinephrine; oxprenolol; propafenone; propoxyphene; quinine-quinidine diastereoisomers; tranylcypromine; verapamil; and propanolol. The stereoselective, clinical pharmacological, and therapeutically active drugs are disclosed in: *Pharmacotherapy*, Vol. 8, pp 147-157, (1988); *Drugs*, Vol. 30, pp 333-354, (1985); *Journal of Pharmaceutical Sciences*, Vol. 78, pp 695-715, (1989); *Clin. Pharmacokinet.*, Vol. 18, pp 339-345, (1990); *Clinical Pharmacology and Therapeutics*, Vol. 40, pp 125-133, (1986); and, *Biopharmaceutics and Drug Disposition*, Vol. 11, pp 507-518, (1990).

Dosage form 10 in first layer 13 and in second layer 14 comprises together about 15 weight percent (wt %) to 96 wt % of a cellulose polymer composition, based on the total weight of the dosage form. In one presently preferred manufacture, the cellulosic composition of dosage form 10 in the respective layer comprises at least on hydroxypropylmethylcellulose or at least on hydroxypropylcellulose. The hydroxypropylmethylcellulose operable for the purpose of this invention comprises a hydroxypropyl content of 4% to 12% and a methyloxy content of 19% to 24%. Exemplary hydroxypropylmethylcelluloses that can be used for forming dosage form 10 comprises at least one of a member selected from the group consisting of (a) a hydroxypropylmethylcellulose having a degree of polymerization (DP) of about 50, a viscosity of about 3 centipoises of a 2% solution in water, a number average molecular weight ($MW_n$) of about 9,200 grams per mole; (b) a hydroxypropylmethylcellulose having a DP of 100, a viscosity of 35 centipoises (cps), $MW_n$ of 19,600; (c) a hydroxypropylmethylcellulose comprising a DP of 145, a viscosity of 100 cps, a $MW_n$ of 27,800; (d) a hydroxypropylmethylcellulose comprising a DP of 690, a viscosity of 15,000 cps, a $MW_n$ of 132,500; and (e) a hydroxypropylmethylcellulose having a DP of 1260, a viscosity of 100,000 cps, and a $MW_n$ of 242,000. Other hydroxypropylmethylcellulose ethers that can be used for the purpose or providing the layers of dosage form 10 are (f) hydroxypropylmethylcellulose comprising a DP of 59, a viscosity of 6, and a $MW_n$ of 11,900; and (g) a hydroxypropylmethylcellulose possessing a DP of 860, a viscosity of 30,000 and a $MW_n$ of 165,000. The examples as set forth above generally comprise a hydroxypropylmethylcellulose comprising a DP of 40 to 1600 a viscosity of 2 to 225,000 and a $MW_n$ of from 9,000 to 307,200. In the specification, DP is the degree of polymerization indicating the number of monomers polymerized in the final polymer, and $MW_n$ is the number average molecular weight of the polymer.

The hydroxypropylcellulose used for the purpose of this invention is a nonionic ether with a neutral pH range, and a hydroxypropyl content of 7% to 16%, with a more specific hydroxypropylcellulose comprising a hydroxypropyl content of 7% to 10%; a hydroxypropyl content of 10% to 13%; and a hydroxypropyl content of 13% to 16%.

First layer 13, in one presently preferred embodiment comprises from 1 wt % to 99 wt % of a single low substituted hydroxypropylcellulose ether polymer comprising a hydroxypropyl content of 7% to 16%, or in an other embodiment first layer 13 comprises from 1 wt % to 70 wt % of hydroxypropylcellulose and 1 wt % to 70 wt % hydroxypropylmethylcellulose with all ingredients in first layer 13 equal to 100 wt %. First layer 13 in other preferred embodiments comprise (a) a stereoisomer drug and a binary blend of hydroxypropylcellulose comprising a hydroxypropyl content of 7 to 10 wt %, blended with a hydroxypropylcellulose having a hydroxypropyl content of 13 to 16 wt %; (b) a composition comprising a stereoisomer drug, a hydroxypropylcellulose having a hydroxypropyl content of 7 to 10 wt %, blended with a hydroxypropylcellulose having a hydroxypropyl content of 10 to 13 wt %; (c) a composition comprising a stereoisomer drug comprising a hydroxypropylcellulose and a hydroxypropylmethylcellulose having a $MW_n$ of 9,200; (d) a composition comprising a stereoisomer drug, a hydroxypropylcellulose and a hydroxypropylmethylcellulose having a $MW_n$ of 19,600; (e) a dosage amount of a stereoisomer drug, a hydroxypropylcellulose and a hydroxypropyl methylcellulose comprising a $MW_n$ of 27,800; (f) a composition forming layer comprising a dosage unit amount of a stereoisomer drug, a hydroxypropylcellulose and a hydroxypropylmethylcellulose having a $MW_n$ of about 88,300; (g) a composition comprising a stereoisomer drug, a hydroxypropylcellulose and a hydroxypropylmethylcellulose having a $MW_n$ of about 132,500; and (h) a composition comprising a stereoisomer drug possessing therapeutic indications, a hydroxypropylcellulose and a hydroxypropylmethylcellulose having a $MW_n$ of about 242,000.

Second layer 14 of dosage form 10 for administering a racemate drug 16 over a prolonged period of up to 24 hours comprises in one embodiment (a) a racemate drug 16 and at least one hydroxypropylmethylcellulose in an amount of 15 wt % to 90 wt % based on the total weight of dosage form 10, or (b) a racemate drug 16 and 1 wt % to 99 wt % of a hydroxypropylmethylcellulose based on the total weight of second layer 14, or a racemic drug and 10 wt % to 99 wt % of a hydroxypropylmethylcellulose and from 10 wt % to 99 wt % of a different hydroxypropylmethylcellulose or a hydroxypropylcellulose with the total weight of all ingredients in the second layer equal to 100 wt %. First layer 13 and second layer 14 can comprise a single cellulose polymer, or a blend of two cellulose polymers, or a tertiary blend comprising three cellulose polymers.

Representative compositions comprising second layer 14 are (a) a composition comprising a racemic drug and a hydroxypropylmethylcellulose having a $MW_n$ of about 242,000; (b) a racemic drug and a hydroxypropylmethylcellulose having a $MW_n$ of about 132,500; (c) a composition comprising a racemic drug and both a hydroxypropylmethylcellulose having a $MW_n$ of 9,200 and a hydroxypropylmethylcellulose having a $MW_n$ of 242,000; (d) a composition comprising a racemic drug and a hydroxypropylmethylcellulose having a $MW_n$ of 19,600 and a hydroxypropylmethylcellulose having a $MW_n$ of about 242,000; (e) a composition comprising a racemic drug and a hydroxypropylmethylcellulose having a $MW_n$ of about 27,800 and a hydroxypropylmethylcellulose having a $MW_n$ of about 242,000; (f) a composition comprising a racemic drug and a hydroxypropylmethylcellulose having a $MW_n$ of 88,300 and a hydroxypropylmethylpropylmethylcellulose cellulose having a $MW_n$ of about 242,000; (g) a composition comprising a racemic and a hydroxypropylmethylcellulose having $MW_n$ of 132,500 and a hydroxypropylcellulose having a $MW_n$ of about 242,000; (h) a composition comprising a racemic drug, a hydroxypropylmethylcellulose having a $MW_n$ of 9,200 a hydroxypropylmethylcellulose having a $MW_n$ of 19,600 and a hydroxypropylmethylcellulose having a $MW_n$ of about 242,000; (i) a composition comprising a racemic drug, a hydroxypropylmethylcellulose having a $MW_n$ of 9,200, a hydroxypropylmethylcellulose comprising $MW_n$ of 88,300 and a hydroxypropylmethylcellulose having a $MW_n$ of about 242,000; (j) a composition comprising a racemic drug, a hydroxypropylmethylcellulose having a $MW_n$ of 19,600, a hydroxypropylmethylcellulose having a $MW_n$ of about 27,800 and a hydroxypropylmethylcellulose having a $MW_n$ of about 242,000. A binary composition comprising two cellulose ether polymers in a presently preferred embodiment comprises a racemic drug and from 1 wt % to 99 wt % of one cellulose ether polymer. A tertiary composition comprises a racemic drug and from 1 wt % to 99 wt % of three different cellulose ether polymers possessing different molecular weights with a total racemic drug cellulose ether polymer content of up to 100 wt % based on the total weight of second layer 14.

Figure 3:
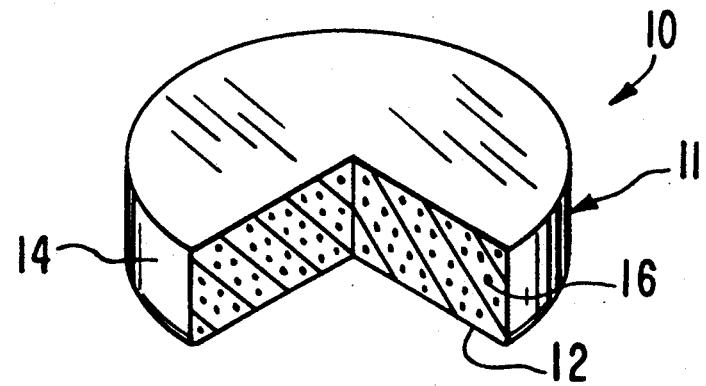
FIG. 3 is an opened view of the dosage form of FIG. 1, which opened view illustrates the dosage form absent the immediate release layer comprising the stereoisomer that was administered from the dosage form leaving the dosage form comprising the prolonged release layer comprising the racemate for administering the racemate to a warm-blooded animal.

FIG. 3 depicts dosage form 10 in opened view at 12. In FIG. 3, first layer 13 comprising stereoisomer drug 15 is not seen because it was administered in a short period of time up to one hour during operation of dosage form 10 in a fluid environment of use. The administration of first layer 13 leaves second layer 14 for delivering over a prolonged period of time up to 24 hours racemate drugs 16. Second layer 14 commences drug delivery on contract by fluid in the environment of use consequently there is overlapping of drug administration from first layer 13 and second layer 14 during the first hour of operation of dosage form 10. The expression fluid environment of use, as used for the purpose of this invention, denotes a biological fluid, or an aqueous fluid.

MODES OF PERFORMING THE INVENTION

Dosage form 10 is manufactured by first making independently first layer 13 or second layer 14. The layers are made from a well-mixed composition of layer forming members. For example, a particular layer is manufactured as follows: first, each of the ingredients comprising a layer are independently screened and then blended together, except for a lubricant. Then, the homogenous blend is wet granulated by adding a solvent such as anhydrous ethanol, and the wet ingredients mixed until a uniform blend is produced by said process. Next, the wet blend is passed through a screen and dried to evaporate the solvent. Next, the resulting granules are again passed through a sieve. Then, a small amount of a finely divided lubricant is added to the drug granules and the lubricant and granules blended to provide a uniform blend. Next, the above described process is repeated for the other layer comprising the dosage form.

Next, the two layers, one layer comprising a single enantiomer, and one layer comprising a racemate consisting of two enantiomers, are independently fed into separate hoppers of a compression machine. The machine lightly compresses one layer-forming granulation, and then adds the second layer-forming granulation in layered arrangement to the first layer and compresses the two layers together. Typically, about two tons of pressure, or more, are applied to laminate the layers and yield the final dosage form.

In another manufacturing embodiment, the dosage form can be made also by a drug granulation process of manufacture. The dry process comprises first mixing for a particular layer, all the layer-forming ingredients, except for the lubricant, passing the mixed ingredients through a grinding mill to a small mesh size, and then transferring the sized powder to a drug compactor. The compactor densifies the powder, which dense powder is then passed through a sizing mill to regrind the composition. The composition is ground to a small size, typically 20 mesh or smaller. Finally, a tabletting lubricant is added and the ingredients blended to produce the final layer-forming composition. The second layer is made in a similar manner. Then, each composition is fed independently to the compaction press and compressed into the dosage form comprising parallel layers.

Other standard manufacturing procedures can be used to form the layer and the bilayered dosage form. For example, the various ingredients can be mixed with a solvent by ballmilling, calendering, stirring or rollmilling, and then pressed into a preselected sized and shaped layer. A second layer made in a like process comprising a shape and size corresponding to the first layer is then layered with pressure to the first layer to yield the bilayered dosage form.

A single stereoisomer, or the racemate can be present in their individual layers neat, or as in a presently preferred optional embodiment, with a binder, dispersant, wetting agent, lubricant or dye. Representatives of these include acacia, agar, calcium carrageenan, alginic acid, algin, agarose powder, collagen, colloidal magnesium silicate, pectin, and gelation; binders like polyvinyl pyrrolidone; lubricants such as calcium stearate, stearic acid, or magnesium stearate; wetting agent such as fatty amines, fatty quaternary ammonium salts, and ester of sorbitol. The phrase "drug formulation" indicates the drug is present in dosage form 10 neat or accompanied by a binder.

Exemplary solvents suitable for manufacturing the individual layers include inorganic and organic solvents that do not adversely harm the layers, the layer forming ingredients and the final dosage form. The solvents broadly include a member selected from the group consisting of aqueous solvents, alcohols, ketones, esters, ethers, aliphatic hydrocarbons, halogenated solvents, cycloaliphatic solvents, aromatic, heterocyclic solvents, and mixtures thereof. Typical solvents include water, acetone, diacetone, methanol, ethanol, isopropyl alcohol, butyl alcohol, methyl acetate, ethyl acetate, isopropyl acetate, n-butylacetate, methyl isobutyl ketone, methyl propyl ketone, n-hexane, h-heptane, methylene dichloride, ethylene dichloride, propylene dichloride, ethyl ether, mixtures such as acetone and ethanol, acetone and methanol, water and acetone, methylene dichloride and methanol, ethylene dichloride and methanol.

The following examples illustrate means and methods for carrying out the present invention. The examples are merely illustrative and they should not be considered as limiting the scope of the invention, as these examples and other equivalents thereof will become more apparent to those versed in the pharmaceutical dispensing art in the light of the present disclosure, the drawing and the accompanying claims.

EXAMPLE 1

A once-a-day dosage form comprising the stereoisomer drug naproxen and the racemate drug naproxen is prepared as follows: first, a layer forming composition comprising 29.5 wt % S-naproxen nonsteroidal anti-inflammatory drug, 69.5 wt % hydroxypropylmethylcellulose having an average molecular weight of 27,800 and 1.0 wt % magnesium stearate are homogeneously blended into a uniform composition and then compressed into a first layer. Next, a second layer forming composition comprising 40 wt % racemic naproxen nonsteroidal anti-inflammatory drug, 57 wt % hydroxypropylmethylcellulose having a molecular weight of 242,000, 1.0 wt % ferric oxide and 2.0 wt % magnesium stearate are blended thoroughly in a standard laboratory V-blender to yield a homogenous composition. The second composition is deposited over the first layer and the second layer compressed onto the first layer at 2 tons pressure to yield a bilayered system. The bilayers are compressed in a 13/32 inch (0.101 cm) die. The dosage form release pattern is measured in a shaking flask containing water and a few marbles for producing mechanical abuse. The first layer comprising the stereoisomer naproxen comprising the lower molecular weight cellulose ether erodes in an aqueous environment and administers the drug over a one hour period. The second layer comprising the racemic naproxen comprising the higher molecular weight cellulose ether maintains its mechanical integrity longer and releases its drug over a prolonged period up to 24 hours.

EXAMPLE 2

The procedure described above is followed in this example. In a first step, a first layer comprising 88 wt % (−) nimodipine, a stereoisomer calcium antagonist, 10 wt % hydroxypropylcellulose with a 10 to 13 wt % hydroxypropyl content and 2 wt % magnesium stearate are blended into a homogenous blend and pressed into a first layer. Next, a second layer is formed comprising 58 wt % racemic nimodipine, a racemic calcium antagonist, 25 wt % hydroxypropylmethylcellulose having a number average molecular weight of 242,000, a viscosity of 100,000 centipoises, 15 wt % hydroxypropylmethylcellulose, having a number average molecular weight of 9,200, a number average degree of polymerization of 50 and a viscosity of 3 centipoises, and 2 wt % stearic acid are thoroughly blended in a standard laboratory blender to yield a homogenous layer-forming composition. The composition is pressed next into a layer, in a layered contacting arrangement with the first layer to yield a bilayer dosage form. The dosage form provides for the immediate release of the stereoisomer over 1 hour and for the release of the racemate over 24 hours.

EXAMPLE 3

The procedure described in the above examples is followed in this example. In this example, the dosage form is prepared as follows: a first layer weighing 230 mg comprising 44 wt % optically pure S-isomer of ibuprofen analgesic, 40 wt % hydroxypropylcellulose with a 11 to 13 wt % average hydroxypropyl content, 14 wt % hydroxypropylmethylcellulose having an average number molecular weight of 9,200 and 2 wt % stearic acid are blended for 10 to 12 minutes in a blender and then pressed into a first layer for immediate analgesic therapy. Next, a second layer composition weighing 690 mg is prepared, comprising 58 wt % racemic ibuprofen, 25 wt % hydroxypropylmethylcellulose having a number average molecular weight of 242,000, 15 wt % hydroxypropylmethylcellulose having a number average molecular weight of 9,200 and 2 wt % stearic acid are blended for 15 minutes to yield a homogenous composition. Next, the second composition is pressed into a second layer in contacting layered arrangement with the first layer, to yield a dosage form. The dosage form in operation in a fluid environment exhibits an initial burst of 100 mg of stereoisomer ibuprofen within the first layer accompanied by the second layer releasing 28 mg per hour for the next eleven hours to provide both stereoisomer ibuprofen therapy and racemate ibuprofen therapy to a patient in need of ibuprofen therapy.

EXAMPLE 4

A dosage form for administering ibuprofen is prepared as follows: first, 5,800 grams of racemic ibuprofen is passed through a screen having 40 wires per inch (420 micron openings Then, 1,500 grams of hydroxypropylmethylcellulose having a number average molecular weight of 254,000 grams per mole, an average hydroxypropoxyl content of 4.0 to 12.0 weight percent and an average methoxyl content of 19.0 to 24.0 weight percent, and 2,500 grams of hydroxypropylmethylcellulose having a number average molecular weigh of 9,600 grams per mole with an average hydroxypropoxyl content of 4.0 to 12.0 weight percent and an average methoxyl content of 19.0 to 24.0 weight percent is passed through a number 40 mesh sieve. The racemic ibuprofen and the hydroxypropylmethylcellulose were mixed for 5 minutes to a uniform blend. Then, anhydrous ethyl alcohol is blended into the mixture to form a damp mass. The damp mass is passed through a sieve having 20 wires per inch (840 micron openings), thereby forming granules. The granules are dried overnight at room temperature. The air-dried granules are then passed again through a sieve with 20 wires per inch. Then, 200 grams of stearic acid, which is passed through a sieve having 80 wires per inch (177 micron openings), is blended into the mixture with 3 minutes of tumbling. This composition is used to form the second, or slow layer granulation of the dosage form.

Then, 8,700 grams of S(+) ibuprofen is passed through a sieve having 40 wires per inch, followed by 1000 g of low substituted hydroxypropoxylcellulose having an average hydroxypropoxyl content of 10.0 to 13.0 weight percent is passed through a 40 mesh sieve. Then 100 g of hydroxypropylmethylcellulose having a number average molecular weight of 9,200 grams per mole comprising a hydroxypropoxyl content of 4.0 to 12.0 weight percent and a methoxyl content of 19.0 to 24.0 weight percent is sieved through a 40 mesh sieve. The 40 mesh S(+) ibuprofen, the hydroxypropylmethylcellulose and the hydroxypropylcellulose are mixed for five minutes to produce a uniform blend. Next, anhydrous ethyl alcohol is blended into the mixture to form a damp mass. the damp mass is passed through a 20 mesh screen to provide damp granules. The granules are dried overnight at ambient temperatures. Then, 200 g of stearic acid, which had previously been sieved through a number 80 mesh sieve, is blended into the mixture with 3 minutes of tumbling. This composition formed the first, or fast layer granulation of the dosage form.

Figure 4:
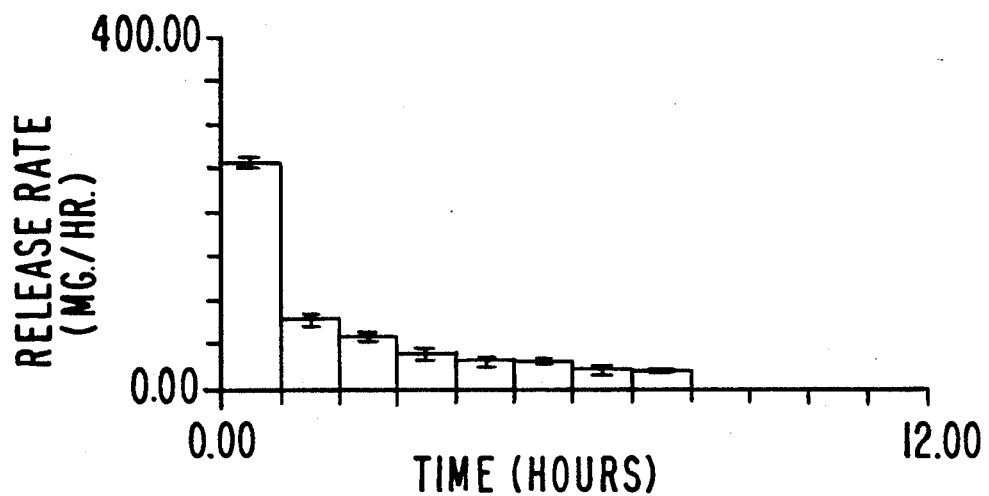
FIG. 4 is a graph that depicts the release rate of drug from a dosage form provide by the invention; and, FIG. 5 is a graph that depicts the cumulative amount of drug released by a dosage form provided by the invention.
Figure 5:
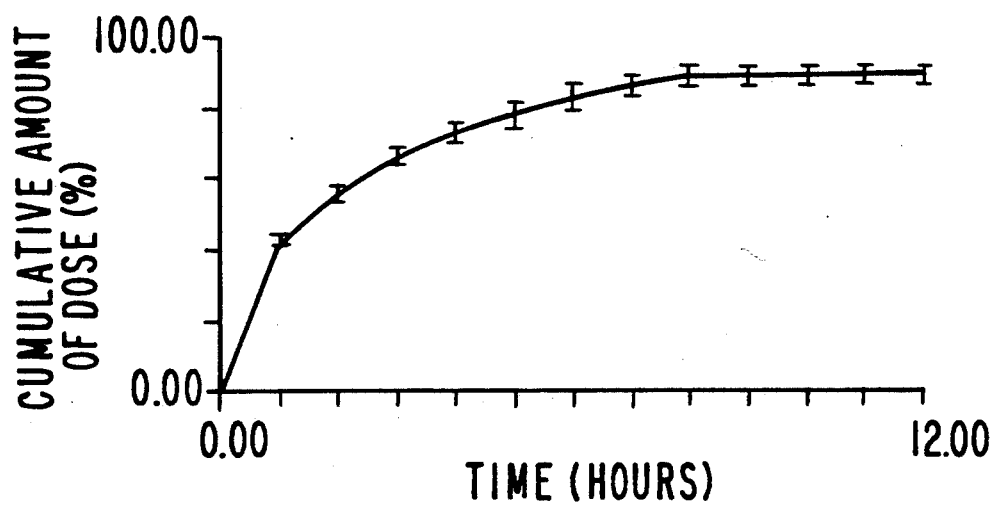

Next, the granulations are fed to a Manesty layer press fitted with two hoppers, one hopper is filled with the slow-layer granulation, the other hopper is filled with the fast-layer granulation. A bilayer tablet dosage form is then compressed by first forming a 690 mg second layer, then a 230 mg first layer is pressed in release retaining relation to the second layer. The first layer and second layers are pressed together under a pressure head of two tons. This manufacturing process produces the bilayer dosage form. Accompanying FIG. 4 illustrates the release rate in mg per hour from the dosage form, and accompanying FIG. 5 depicts the cumulative amount of medicament released over time. The final composition of the first layer is 87 wt % S(+) ibuprofen, 10 wt % low substituted hydroxypropylcellulose, 2 wt % stearic acid and 1 wt % hydroxypropylmethylcellulose having a molecular weight of 9,200. The final composition of the second layer comprises 58 wt % racemic (±) ibuprofen, 15 wt % hydroxypropylmethylcellulose having a 242,000 molecular weight, 25 wt hydroxypropylmethylcellulose having a 9,200 molecular weight and 2 wt % stearic acid. The S(+) ibuprofen used for the purpose of this example exhibited a melting point of 51°-52° C.; a bulk density of 0.277 g/cc; a tapped density of 0.391 g/cc; a tablet density of 1.038 g/cc; an optical rotation of 57.7 degrees; a solubility in mg/ml at 37° C. in AGF, artificial gastric juice of 0.131, in AIF, artificial intestinal juice, of 6.98, and in water 0.134; and, a crystal lattice energy of 90.3 joules/g. The racemic ibuprofen used for the purposes of this example exhibited a melting point of 75°-80° C.; a bulk density of 0.328 g/cc; a tapped density of 0.483 g/cc; a tablet density of 1.052 g/cc; an optical rotation of 0 degrees; a solubility in mg/ml at 37° C., in AGF of 0.079, in AIF, of 5,91, in water of 0.082; and a crystal lattice energy of 117 joules/g.

EXAMPLE 5

A dosage form for the controlled immediate release and for the controlled continuous release of the drug stereoisomer (S) sulindac nonsteroidal anti-inflammatory drug is prepared following the above described process of manufacture. The dosage form is manufactured by making a first layer comprising 49 wt % of (S) sulindac, 49 wt % low molecular weight hydroxypropylmethylcellulose having an average number molecular weight of 19,600, 1 wt % stearic acid and 1 wt % lightly crossedlinked polyvinylpyrrolidone; and a second layer comprising 65 wt % (±) racemic sulindac, 1 wt % hydroxypropylcellulose with a 12 wt % hydroxypropoxyl content, 33 wt % hydroxypropylmethylcellulose having an average number molecular weight of 242,000, and 1 wt % magnesium stearate. The two layers operate as a unit dosage form for release of the stereoisomer and the racemate at controlled rate in different times for the intended therapy.

EXAMPLE 6

A dosage form comprising two separate and distinct modes of drug delivery comprising for the immediate release of stereoisomer flurbiprofen and for the slow controlled release over time or racemic flurbiprofen is prepared by following the above examples. The dosage form provided by this example comprises a first layer, or instant-release layer of 50 mg of stereoisomer flurbiprofen consists of a hydrophilic polymer that absorbs fluid, swells, hydrates rapidly when exposed to an aqueous fluid and releases the drug. The slow release layer comprises 250 mg of racemic flurbiprofen and a slow hydrating polymer for release of the racemic drug over time. The two layers are compressed into a single, bilayer tablet. When administered orally to a patient in need of analgesic therapy, the instant-release layer would make the drug readily available to the patient, and the slow release layer would release slowly over 10 to 18 hours the drug. The dosage form is manufactured by making a first layer containing 50 mg of stereoisomer flurbiprofen, 49 mg of low molecular weight hydroxypropylmethylcellulose having an average number molecular weight of 27,000 and 1 mg of magnesium stearate; and a second layer comprising 250 mg of racemic flurbiprofen, 7.50 mg hydroxypropylcellulose having a 13 wt % hydroxypropoxyl content, 300 mg hydroxypropylmethylcellulose having a molecular weight of 242,000, 10 mg ferric oxide and 10 mg of magnesium stearate.

EXAMPLES 7-10

The procedures described above are followed for manufacturing dosage forms comprising the following: 50 mg of (s) methyldopamine in the first layer and 150 mg racemic methyldopamine in the second layer; 75 mg (−)atenolol in the first layer and 150 mg racemic atenolol in the second layer; 15 ng (−)fentanyl in first layer and 75 ng of racemic fentanyl in the second layer; and 40 mg (d) brompheniramine and 80 mg of racemic brompheniramine in the second layer.

MODE OF USING THE INVENTION

The present invention provides unexpected therapeutic advantages, for example, (a) the isomeric drug is metabolized differently than the racemic drug which differences in properties can be used to produce different therapeutic responses in the animal body, (b) the invention makes it possible to contain in a single dosage form a layer comprising a racemate which tends to be a crystalline solid with higher crystal lattice energy and exhibits good cohesive properties, and a layer comprising an optical isomer which may possess low crystal lattice energy or is amorphous. These crystalline structure differences of the isomer and the racemate lead away from the separate lamination of one to the other as unexpectedly effected herein.

The invention provides additional therapeutic advantages, for example, (c) the fast drug releasing begins to dispense isomeric drug immediately for producing an initial plasma concentration of drug in a warm-blooded animal, which expression includes humans. The slower drug releasing layer releases racemic drug continuously and over time for producing a steady-state racemic drug concentration. The expressions "fast drug releasing layer" and "slower drug releasing layer" as used for the purpose of this invention, denotes that first layer releases isomeric drug at a faster rate per unit time than does the slow, racemic layer. Also, because of its physical properties, the slow releasing drug layer provides mechanical support for the first layer. Another advantage provided by dosage form 10 is that it exhibits stomach retention during part of its drug releasing life. The stomach retention provides release of isomeric drug in the stomach for drug absorption in the upper gastrointestinal tract. This retention in the upper gastrointestinal tract and delivery of isomeric drug from the stomach allows the isomeric and then the racemic drug to be absorbed throughout the gastrointestinal tract. This delivery system is particularly useful for drugs with known absorption windows in the upper tract.

Additional advantages of dosage form 10 are its release of isomeric and racemic drug at a rate independent of the pH of the environment of use. Dosage form 10 releases either drug at about the same rate per unit time in artificial stomach fluid and in artificial intestinal fluid. Dosage form 10 releases either drug substantially free of irritating laboratory mucosal tissue. Eventually dosage form 10 fully erodes and dissolves in the gastrointestinal tract substantially free of residual particles.

An embodiment of using the invention pertains to a method for delivering a stereoisomer and a racemate to an animal in need of therapy. The method comprises admitting orally a dosage form, shaped, sized and adapted for admittance into the gastrointestinal tract, wherein the method comprises the steps of: (A) admitting orally into an animal a dosage form comprising: (1) a first layer comprising a dosage amount of a stereoisomer drug; (2) a second layer comprising a racemic drug; (B) releasing the isomeric drug from the first layer in from zero minutes to sixty minutes to provide immediate therapy; and, (c) releasing the racemate drug from the second layer in from zero minutes to twenty-four hours to provide prolonged therapy; whereby, (D) immediate therapy and prolonged therapy are provided from the same dosage form.

The novel devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions and omissions in the devices illustrated and described can be made without departing from the spirit of the invention.

We claim:

1. An improvement in a method for administering a drug to a patient in need of therapy, wherein the method comprises:
    (a) admitting orally into the patient a dosage form comprising:
        (1) a first layer comprising 0.10 ng to 500 mg of stereoisomer drug and from 1 wt % to 99 wt % of a hydroxypropylmethylcellulose;
        (2) a second layer comprising 1 mg to 650 mg of a racemic drug and 1 wt % to 99 wt % of a different hydroxypropylmethylcellulose; and wherein the improvement comprises:
    (b) releasing the stereoisomer drug over a period of instant release up to 1 hour from the first layer to provide instant stereoisomeric drug therapy to the patient; and, (c) releasing the racemic drug over a prolonged period up to 24 hours from the second layer to provide prolonged racemic drug therapy to the patient.

2. An improvement in a method for administering a drug to a patient in need of therapy according to claim 1, wherein the stereoisomer durg is ibuprofen.

3. An improvement in a method for administering a drug to a patient in need of therapy according to claim 1, wherein the stereoisomeric drug is a member selected from the group consisting of a stereoisomer drug that acts on a peripheral nerve, adrenergic receptor, cholinergic receptor, nervous system, skeletal muscle, cardiovascular system, smooth muscle, blood circulatory system, synaptic sites, neuroeffector junctional sites, endocrine system, hormone system, immunological system, reproductive system, autocoid system, alimentary system, excretory system, patient organs, patient body passageways, and the autocoid system.

4. A method for administering a drug stereoisomer and a drug racemate to a patient in need of drug therapy, wherein the method comprises:
(a) admitting a dosage form orally into the patient, said dosage form comprising
  (1) a first layer comprising 0.10 ng to 500 mg of a drug stereoisomer and from 1 wt % to 99 wt % of a pharmaceutically acceptable hydroxypropylcellulose;
  (2) a second layer comprising 1 ng to 650 mg of a drug racemate and from 1 wt % to 99 wt % of a pharmaceutically acceptable hydroxypropylmethylcelulose;
(b) administering the drug stereoisomer over a short period of time from the first layer;
(c) administering the drug racemate over a longer period of time from the second layer; whereby
(d) therapy is provided to the patient over both a short period and a longer period of time.

* * * * *